(12) United States Patent
Kimura et al.

(10) Patent No.: US 11,117,849 B2
(45) Date of Patent: Sep. 14, 2021

(54) METHOD FOR PRODUCING INDENE

(71) Applicant: ENEOS Corporation, Tokyo (JP)

(72) Inventors: Nobuhiro Kimura, Tokyo (JP); Atsushi Segawa, Tokyo (JP)

(73) Assignee: ENEOS CORPORATION, Tokyo (JP)

( * ) Notice: Subject to any disclaimer, the term of this patent is extended or adjusted under 35 U.S.C. 154(b) by 0 days.

(21) Appl. No.: 16/978,913

(22) PCT Filed: Jan. 8, 2019

(86) PCT No.: PCT/JP2019/000251
§ 371 (c)(1),
(2) Date: Sep. 8, 2020

(87) PCT Pub. No.: WO2019/176248
PCT Pub. Date: Sep. 19, 2019

(65) Prior Publication Data
US 2021/0047248 A1 Feb. 18, 2021

(30) Foreign Application Priority Data
Mar. 13, 2018 (JP) .............................. JP2018-045606

(51) Int. Cl.
C07C 5/333 (2006.01)
B01J 23/14 (2006.01)
B01J 23/42 (2006.01)
B01J 21/00 (2006.01)
B01J 21/10 (2006.01)
B01J 23/62 (2006.01)
C07C 5/367 (2006.01)

(52) U.S. Cl.
CPC ........... C07C 5/3337 (2013.01); B01J 21/005 (2013.01); B01J 21/10 (2013.01); B01J 23/14 (2013.01); B01J 23/626 (2013.01); C07C 5/367 (2013.01); C07C 2521/04 (2013.01); C07C 2521/10 (2013.01); C07C 2523/14 (2013.01); C07C 2523/62 (2013.01)

(58) Field of Classification Search
None
See application file for complete search history.

(56) References Cited

U.S. PATENT DOCUMENTS

| 4,143,082 | A | 3/1979 | Bartek et al. |
| 4,568,783 | A | 2/1986 | Pedersen et al. |
| 6,380,450 | B1 | 4/2002 | Matsumura |
| 9,580,368 | B2 * | 2/2017 | Chen ...................... C07C 5/325 |
| 2004/0013728 | A1 | 1/2004 | Oh et al. |
| 2004/0266612 | A1 | 12/2004 | Hayes et al. |

FOREIGN PATENT DOCUMENTS

| CZ | 135251 | 7/1969 |
| JP | 54-39060 | 3/1979 |
| JP | 2000-063298 A | 2/2000 |
| JP | 2000-063299 A | 2/2000 |
| JP | 2002-320857 A | 11/2002 |
| JP | 2004-537407 A | 12/2004 |
| JP | 2010-104967 A | 5/2010 |
| JP | 2013-133293 A | 7/2013 |
| JP | 2017-189754 A | 10/2017 |
| JP | 2017-210461 A | 11/2017 |
| WO | 03/013728 A2 | 2/2003 |

OTHER PUBLICATIONS

ISR issued in WIPO Patent Application No. PCT/JP2019/000251, dated Apr. 9, 2019, English translation.
Written Opinion of Int'l Search Authority issued in WIPO Patent Application No. PCT/JP2019/000251, dated Apr. 9, 2019.
IPRP issued in WIPO Patent Application No. PCT/JP2019/000251, dated Sep. 24, 2020, English translation.

* cited by examiner

*Primary Examiner* — Philip Y Louie
(74) *Attorney, Agent, or Firm* — Greenblum & Bernstein, P.L.C.

(57) ABSTRACT

The present invention provides a production method for indene, comprising a dehydrogenation step of obtaining a reaction product containing indene by contacting a raw material composition containing indene with a dehydrogenation catalyst, wherein the dehydrogenation catalyst comprises a support containing aluminum, and a group 14 metal element and platinum supported on the support, a content of the platinum in the dehydrogenation catalyst is 0.6 to 2.5% by mass based on a whole amount of the dehydrogenation catalyst, and an atomic ratio of the group 14 metal element to the platinum in the dehydrogenation catalyst is 4.0 to 20.0.

6 Claims, No Drawings

METHOD FOR PRODUCING INDENE

TECHNICAL FIELD

The present invention relates to a production method for indene.

BACKGROUND ART

Indene is an industrially useful substance as a material of a coumarone-indene resin or an optical resin. As a method for producing indene, a method for collecting indene from a coal tar distillate is known, but since a coal tar distillate contains a large number of impurities such as benzonitrile and benzofuran, when a separation/collection method through distillation is employed, it is difficult to obtain indene with high impurity particularly with benzonitrile having a close boiling point separated. Alternatively, as a method for producing indene, a method for directly obtaining indene by dehydrogenation reaction of tetrahydroindene is known (Patent Literatures 1 to 3).

CITATION LIST

Patent Literature

Patent Literature 1: Japanese Unexamined Patent Publication No. 2000-63298
Patent Literature 2: Japanese Unexamined Patent Publication No. 2000-63299
Patent Literature 3: Japanese Unexamined Patent Publication No. 2013-133293

SUMMARY OF INVENTION

Technical Problem

An object of the present invention is to provide, as a novel production method for indene, a production method for indene in which a side reaction is minimally caused and indane can be efficiently dehydrogenated.

Solution to Problem

The present inventors have found that a specific dehydrogenation catalyst exhibits excellent dehydrogenation activity and high indene selectivity in dehydrogenation reaction of indane, resulting in accomplishing the present invention.

One aspect of the present invention relates to a production method for indene comprising a dehydrogenation step of obtaining a reaction product containing indene by contacting a raw material composition containing indane with a dehydrogenation catalyst. In this production method, the dehydrogenation catalyst comprises a support containing aluminum, and a group 14 metal element and platinum supported on the support, a content of the platinum in the dehydrogenation catalyst is 0.6 to 2.5% by mass based on the whole amount of the dehydrogenation catalyst, and an atomic ratio of the group 14 metal element to the platinum in the dehydrogenation catalyst is 4.0 to 20.0.

In the production method, a specific dehydrogenation catalyst is used. Thus, a side reaction is adequately inhibited in the production method, and hence, indane can be efficiently dehydrogenated and indene can be obtained with high efficiency.

In one aspect, the atomic ratio of the group 14 metal element to the platinum in the dehydrogenation catalyst may be 7.0 to 20.0.

In one aspect, the group 14 metal element may be tin.

In one aspect, the group 14 metal element and the platinum may be supported on the support by using a metal source not containing a chlorine atom.

In one aspect, a mole fraction of the indane in the raw material composition may be 0.2 or more.

In one aspect, the production method may further comprise a raw material synthesis step of obtaining indane by dehydrogenation reaction of tetrahydroindene.

Advantageous Effects of Invention

According to the present invention, a production method for indene in which a side reaction is minimally caused and indane can be efficiently dehydrogenated is provided as a novel production method for indene.

DESCRIPTION OF EMBODIMENTS

Now, a preferred embodiment of the present invention will be described. It is noted that the present invention is not limited to the following embodiment at all.

A production method for indene of the present embodiment comprises a dehydrogenation step of obtaining a reaction product containing indene by contacting a raw material composition containing indane with a dehydrogenation catalyst.

In the present embodiment, the dehydrogenation catalyst comprises a support containing aluminum, and a group 14 metal element and platinum supported on the support. Besides, in the present embodiment, a content of platinum in the dehydrogenation catalyst is 0.6 to 2.5% by mass based on the whole amount of the dehydrogenation catalyst, and an atomic ratio of the group 14 metal element to platinum in the dehydrogenation catalyst is 4.0 to 20.0.

In the production method of the present embodiment, since a specific dehydrogenation catalyst is used, a conversion rate of indane and selectivity of indene in dehydrogenation reaction are increased, and hence, indene can be efficiently obtained, and dehydrogenation efficiency of indane is improved.

Now, the dehydrogenation catalyst of e present embodiment will be described in detail.

The dehydrogenation catalyst used in the present embodiment is a catalyst comprising a support containing aluminum, and a group 14 metal element and platinum supported on the support. Here, a group 14 metal element means a metal element belonging to the group 14 of the long-form periodic table of elements based on the definition of IUPAC (International Union of Pure and Applied Chemistry). Examples of the group 14 metal element include tin (Sn) and lead (Pb).

A method for preparing the dehydrogenation catalyst is not especially limited, and may be a method in which the group 14 metal element is caused to be supported on the support, and then platinum is further caused to be supported thereon, a method in which platinum is caused to be supported on the support, and then the group 14 metal element is further caused to be supported thereon, or a method in which the group 14 metal element and platinum are simultaneously caused to be supported on the support.

In the dehydrogenation catalyst, each of the support containing aluminum, the group 14 metal element and platinum may be present in the form of an oxide, may be present in the form of a complex oxide with another metal, or may be present in the form of a metal salt or a metal simple substance.

The dehydrogenation catalyst may comprise another metal element in addition to aluminum, the group 14 metal element and platinum. Examples of another metal element include lithium. (Li), sodium (Na), potassium (K), magnesium (Mg), calcium (Ca), zin (Zn), iron (Fe), indium (In), selenium (Se), antimony (Sb), nickel (Ni), and gallium (Ga).

In one aspect, the dehydrogenation catalyst may be a catalyst in which a supported metal including the group 14 metal element and platinum is supported on the support containing aluminum. In another aspect, the dehydrogenation catalyst may be a catalyst in which a supported metal including platinum is supported on a support containing aluminum and the group 14 metal element.

The support is preferably an inorganic oxide support containing aluminum. An inorganic oxide containing aluminum may be an oxide singly containing aluminum as a metal, or may be a complex oxide of aluminum with another metal. The oxide singly containing aluminum as a metal may be, for example, alumina ($Al_2O_3$). The complex oxide of aluminum and another metal may be, for example, a complex oxide of aluminum and magnesium (Mg), a complex oxide of aluminum and tin (Sn), a complex oxide of aluminum and lead (Pb), or a complex oxide of aluminum, and zinc (Zn), selenium (Se), iron (Fe), indium (In) or the like.

An example of the inorganic oxide support containing aluminum includes a support containing an inorganic oxide such as alumina, alumina magnesia, silica alumina, zirconia alumina, or a spinel structure (magnesium spinel).

A content of aluminum in the support may be 25% by mass or more, and is preferably 50% by mass or more based on the whole amount of the support.

A specific surface area of the support may be, for example, 30 $m^2/g$ or more, and is preferably 50 $m^2/g$ or more. Thus, the effect of increasing the conversion rate of indane can be exhibited. The specific surface area of the support may be, for example, 1000 $m^2/g$ or less, and is preferably 500 $m^2/g$ or less. Thus, a support having sufficient strength to be suitably industrially applicable can be obtained. It is noted that the specific surface area of the support is herein measured with a BET specific surface area meter employing a nitrogen adsorption method.

A method for preparing the support is not especially limited, and examples include a sol-gel method, a coprecipitation method, and a hydrothermal method.

A content of platinum in the dehydrogenation catalyst is 0.6 to 2.5% by mass based on the whole amount of the dehydrogenation catalyst. An amount of platinum supported is preferably 0.7% by mass or more based on the whole amount of the dehydrogenation catalyst. The amount of platinum supported is preferably 2.0% by mass or less based on the whole amount of the dehydrogenation catalyst. When such an amount supported is employed, a platinum particle to be formed on the catalyst can be easily made to have a size suitable for the dehydrogenation reaction, and a platinum surface area per unit platinum weight is increased, and therefore, a more efficient reaction system can be realized.

An atomic ratio of the group 14 metal element to platinum in the dehydrogenation catalyst is 4.0 to 20.0, and preferably 7.0 to 20.0. The ratio is more preferably 18.0 or less. When the ratio falls in the aforementioned range, a side reaction is more remarkably inhibited, and in addition, the conversion rate of indane tends to be further improved.

A content of the group 14 metal element in the dehydrogenation catalyst is not especially limited, and may be appropriately changed, for example, in a range satisfying the above-described ratio. An amount of the group 14 metal element supported is, for example, 1.5% by mass or more, and preferably 2.5% by mass or more based on the whole amount of the dehydrogenation catalyst. The amount of the group 14 metal element supported is, for example, 25% by mass or less, and preferably 15% by mass or less based on the whole amount of the dehydrogenation catalyst.

The group 14 metal element may be, for example, at least one selected from the group consisting of germanium (Ge), tin (Sn), and lead (Pb). Among these, when the group 14 metal element is tin, the effects of the present invention are further remarkably exhibited.

The dehydrogenation catalyst may be one obtained by causing platinum and tin to be supported on the support by using a platinum source and a tin source. Examples of the platinum source include tetraammineplatinous(II) acid, tetraammineplatinum(II) acid salt (such as nitrate), a tetraammineplatinous(II) hydroxide solution, a dinitrodiammineplatinous(II) nitric acid solution, a hexahydroxoplatinic(IV) nitric acid solution, and a hexahydroxoplatinic(IV) ethanolamine solution. Examples of the tin source include sodium stannate and potassium stannate. As each of the platinum source and the tine source, a metal source not containing a chlorine atom is preferably used. When a metal source not containing a chlorine atom is used, corrosion of an apparatus used can be inhibited, and indane can be more efficiently dehydrogenated.

A supporting method for a supported metal is not especially limited, and examples include an impregnation method, a deposition method, a coprecipitation method, a kneading method, an ion exchange method, and a pore filling method.

One aspect of the supporting method will now be described. First, a support is added to a solution containing precursors (a group 14 metal element source and a platinum source) of supported metals, and the resultant support containing the solution is kneaded. Thereafter, a solvent is removed by drying, the thus obtained solid is baked, and thus, the supported metals can be supported on the support.

Baking can be performed, for example, in an air atmosphere or in an oxygen atmosphere. The baking may be performed in single stage, or in multiple stages of two or more stages. A baking temperature may be a temperature at which the precursors of the supported metals can be decomposed, and for example, may be 200 to 1000° C., or may be 400 to 800° C. Incidentally, when the baking is performed in multiple stages, the baking temperature may be employed in at least one of the stages. Baking temperatures employed in the other stages may be, for example, in the same range as described above, or may be 100 to 200° C.

The dehydrogenation catalyst may be molded by a method such as an extruding method or a tableting method.

From the viewpoint of improvement of moldability, dehydrogenation catalyst may further contain a molding aid as long as the physical properties and catalytic performance of the catalyst are not impaired. The molding aid may be, for example, at least one selected from the group consisting of a thickener, a surfactant, a water retention agent, a plasticizer, and a binder material. A molding step of molding the dehydrogenation catalyst may be performed at a suitable stage in the production process of the dehydrogenation catalyst in consideration of the reactivity of the molding aid.

A shape of the dehydrogenation catalyst is not especially limited, and can be appropriately selected in accordance with a form in which the catalyst is used. The shape of the dehydrogenation catalyst may be, for example, a pellet shape, a granular shape, a honeycomb shape, or a sponge shape.

The dehydrogenation catalyst may be subjected, before use, to a reduction treatment as a pretreatment. The reduction treatment can be performed, for example, by holding the dehydrogenation catalyst in a reducing gas atmosphere at 40 to 600° C. A holding time may be, for example, 0.05 to 24 hours. The reducing gas may contain, for example, hydrogen or carbon monoxide. When the dehydrogenation catalyst having been subjected to the reduction treatment is used, an initial induction period of the dehydrogenation reaction can be shortened. The initial induction period of the dehydrogenation reaction refers to a state where a very small amount of a supported metal contained in a dehydrogenation catalyst has been reduced to be placed in an active state such that the activity of the catalyst is low.

Next, the dehydrogenation step of the present embodiment will be described in detail.

In the production method of the present embodiment, the raw material composition containing indane is contacted with the dehydrogenation catalyst in the dehydrogenation step. Thus, indane is dehydrogenated to obtain a reaction product containing indene.

The raw material composition may further contain another component in addition to indane. For example, the raw material composition may further contain an inert gas such as nitrogen or argon, steam, hydrogen, oxygen, carbon monoxide, a carbon dioxide gas, an alkane, an olefin, or the like.

When the raw material composition contains another component in addition to indane, a mole fraction of indane in the raw material composition is preferably 0.1 or more, and more preferably 0.2 or more. An upper limit of the mole fraction of indane in the raw material composition is not especially limited, and may be, for example, 0.95 or less, and is preferably 0.9 or less. When another component is contained in addition to indane, the dehydrogenation reaction tends to easily proceed to inhibit activity degradation of the catalyst. But a large amount of energy is necessary for heating this component, and hence the amount of the component needs to be adequate from an industrial viewpoint. When the mole fraction of indane in the raw material composition falls in the above-described range, energy necessary for the dehydrogenation reaction is further restrained, and hence indane can be efficiently dehydrogenated.

The dehydrogenation step may be performed, for example, by using a reactor filled with the dehydrogenation catalyst, and by causing the raw material composition to pass through the reactor. As the reactor, any of various reactors used for a gas phase reaction using a solid catalyst can be used. Examples of the reactor include a fixed bed adiabatic reactor, a radial flow reactor, and a tubular reactor.

A reaction method for the dehydrogenation may be, for example, a fixed bed method, a moving bed method, or a fluidized bed method. Among these, the fixed bed method is preferred from the viewpoint of equipment cost.

A temperature at which the raw material composition is contacted with the dehydrogenation catalyst is a reaction temperature of the dehydrogenation, and can be said as a temperature within the reactor. From the viewpoint of reaction efficiency, the reaction temperature of the dehydrogenation may be 350 to 800° C., may be 400 to 700° C., or may be 450° C. to 650° C. When the reaction temperature of the dehydrogenation reaction is 350° C. or more, the yield of indene tends to be further improved because equilibrium conversion of indane is not too low. When the reaction temperature of the dehydrogenation reaction is 800° C. or less, the dehydrogenation catalyst tends to retain its high activity for a longer period of time because a coking rate is not too high.

A pressure at which the raw material composition is contacted with the dehydrogenation catalyst, namely, an atmospheric pressure within the reactor, may be 0.01 to 4.0 MPa, may be 0.03 to 0.5 MPa, or may be 0.01 to 0.3 MPa. When the reaction pressure falls in the above-described range, the dehydrogenation reaction tends to easily proceed to obtain further excellent reaction efficiency.

When the dehydrogenation step is performed by a continuous reaction method for continuously supplying the raw material, a liquid hourly space velocity (hereinafter referred to as the "LHSV") may be 0.01 $h^{-1}$ or more, or may be 0.1 $h^{-1}$ or more. When such an LHSV is employed, the conversion rate of indane can be further increased. The LHSV may be 100 $h^{-1}$ or less, or may be 20 $h^{-1}$ or less. When the LHSV falls in the above-described range, the reactor size can be further reduced. Here, the LHSV refers to a ratio (F/L) of a supply rate (amount supplied/time) F of the raw material to the volume L of the dehydrogenation catalyst in a continuous reaction device. It is noted that further preferable ranges of amounts of the raw material and the catalyst used may be appropriately selected in accordance with reaction conditions, the activity of the catalyst and the like, and the LHSV is not limited to the above-described range.

The production method of the present embodiment may further include the raw material synthesis step of obtaining indane by dehydrogenation reaction of tetrahydroindene. In such a production method, the reactor may be further filled with a catalyst other than the dehydrogenation catalyst (hereinafter sometimes referred to as the "second dehydrogenation catalyst").

For example, in the present embodiment, an upstream stage of the second dehydrogenation catalyst in the reactor may be further filled with a solid catalyst (hereinafter sometimes referred to as the "first dehydrogenation catalyst") catalyzing the dehydrogenation reaction from tetrahydroindene to indane. Since the second dehydrogenation catalyst is excellent particularly in the reaction activity of the dehydrogenation reaction from indane to indene, when the upstream stage of the second dehydrogenation catalyst is filled with the first dehydrogenation catalyst, indene can be more efficiently produced from tetrahydroindene.

As the first dehydrogenation catalyst, any one of catalysts for dehydrogenation reaction of tetrahydroindene can be used without any limitation. As the first dehydrogenation catalyst, for example, a chromium/$Al_2O_3$ catalyst, a platinum/$Al_2O_3$ catalyst and a Fe—K catalyst, which are used as catalysts for dehydrogenation reaction, or a Bi—Mo catalyst usually used as a catalyst for oxidative dehydrogenation reaction can be used.

As described so far, according to the production method of the present embodiment, a side reaction is minimally caused, and dehydrogenation can be performed with high indene selectivity Therefore, when the production method of the present embodiment is employed, indene can be efficiently produced from indane. Besides, since chlorine is not contained in the catalyst, this method is suitable for industrial production. For these reasons, the production method of the present embodiment is very useful when indene is industrially produced.

EXAMPLES

Now, the present invention will be more specifically described with reference to examples, and it is noted that the present invention is not limited to these examples.

Catalyst Synthesis Example 1

<Preparation of Support>

20.0 g of commercially available γ-alumina (manufactured by JGC Catalysts and Chemicals Ltd.) was mixed with an aqueous solution obtained by dissolving 25.1 g of magnesium nitrate hexahydrate (manufactured by Wako Pure Chemical Industries Ltd., $Mg(NO_3)_2.6H_2O$) in 150 ml of water. An evaporator was used to stir the thus obtained mixture at 50° C. for 180 minutes, and then remove water therefrom under reduced pressure. Thereafter, the resultant was dried at 130° C. overnight, and then baked at 550° C. for 3 hours, and subsequently at 800° C. for 3 hours. The thus obtained baked product was mixed with an aqueous solution obtained by dissolving 25.1 g of magnesium nitrate hexahydrate (manufactured by Wako Pure Chemical Industries Ltd., $Mg(NO_3)_2.H_2O$) in 150 ml of water, and an evaporator was used to stir the thus obtained mixture at 50° C. for 180 minutes, and then remove water therefrom under reduced pressure. Thereafter, the resultant was dried at 130° C. overnight, and then baked at 550° C. for 3 hours, and subsequently at 800° C. for 3 hours. In this manner, an alumina-magnesia support having a spinel structure was obtained. It is noted that the alumina-magnesia support thus obtained was found to have a diffraction peak derived from Mg spinel at 2θ of 36.9, 44.8, 59.4, and 65.3 degrees through X-ray diffraction measurement (X-ray source: CuKα, apparatus: RINT 2500, manufactured by Rigaku Corporation).

<Preparation of Dehydrogenation Catalyst>

5.0 g of the alumina-magnesia support was mixed with an aqueous solution obtained by dissolving 0.37 g of sodium stannate (manufactured by KISHIDA CHEMICAL Co., Ltd., $Na_2SnO_3.3H_2O$) in 10 ml of water, so as to impregnation support tin in such a manner that a final content of tin after a dehydrogenation catalyst was prepared was 2.7% by mass. Thereafter, the resultant was dried at 130° C. overnight, and then baked at 550° C. for 3 hours, followed by repeatedly washing with water. Subsequently, a dinitrodiammineplatinous(II) nitric acid solution (manufactured by TANAKA Kikinzoku Kogyo K.K., $[Pt(NH_3)_2(NO_2)_2]/HNO_3$) was used to impregnation support platinum in such a manner that a content of platinum was 1.0% by mass, and the resultant was dried at 130° C. overnight, and then baked at 550° C. for 3 hours to obtain a dehydrogenation catalyst A-1.

Catalyst Synthesis Example 2

A catalyst was prepared in the same manner as in Catalyst Synthesis Example 1 except that tin was supported in such a manner that a content of tin was 3.7% by mass, and thus, a dehydrogenation catalyst A-2 was obtained.

Catalyst Synthesis Example 3

A catalyst was prepared in the same manner as in Catalyst Synthesis Example 1 except that tin was supported in such a manner that a content of tin was 5.5% by mass, and thus, a dehydrogenation catalyst A-3 was obtained.

Catalyst Synthesis Example 4

A catalyst was prepared in the same manner as in Catalyst Synthesis Example 1 except that tin and platinum were supported in such a manner that a content of tin was 8.3% by mass and a content of platinum was 3.0% by mass, and thus, a dehydrogenation catalyst B-1 was obtained.

Catalyst Synthesis Example 5

A catalyst was prepared in the same manner as in Catalyst Synthesis Example 1 except that tin and platinum were supported in such a manner that a content of tin was 1.8% by mass and a content of platinum was 1.0% by mass, and thus, a dehydrogenation catalyst B-2 was obtained.

Catalyst Synthesis Example 6

A catalyst was prepared in the same manner as in Catalyst Synthesis Example 1 except that tin and platinum were supported in such a manner that a content of tin was 1.4% by mass and a content of platinum was 0.5% by mass, and thus, a dehydrogenation catalyst B-3 was obtained.

Catalyst Synthesis Example 7

<Preparation of Support>

10.0 g of commercially available γ-alumina (manufactured by JGC Catalysts and Chemicals Ltd.) was mixed with an aqueous solution obtained by dissolving 4.14 g of sodium stannate (manufactured by KISHIDA CHEMICAL Co., Ltd., $Na_2SnO_3.3H_2O$) in 60 ml of water in advance, an evaporator was used to stir the resultant at 50° C. for 30 minutes, and then remove water therefrom under reduced water, so as to impregnation support tin in such a manner that a content of tin was 15.6% by mass. Thereafter, the resultant was dried at 130° C. overnight, and then baked at 550° C. for 3 hours, followed by repeatedly washing with water, and thus, an alumina-tin oxide support was obtained.

<Preparation of Dehydrogenation Catalyst>

A dinitrodiammineplatinous(II) nitric acid solution (manufactured by TANAKA Kikinzoku Kogyo K.K., $[Pt(NH_3)_2(NO_2)_2]/HNO_3$) was used to impregnation support platinum, on the alumina-tin oxide support obtained as described above, in such a manner that a content of platinum was 1.0% by mass, and the resultant was dried at 130° C. overnight, and then baked at 550° C. for 3 hours to obtain a dehydrogenation catalyst B-4.

Example 1

A tubular reactor was filled with 3.7 cc of the dehydrogenation catalyst A-1, and a reaction tube was connected to a fixed bed flow reaction device. The reaction tube was heated to 520° C., and with the temperature kept, hydrogen was allowed to pass therethrough at 99 mL/min for 30 minutes. Subsequently, with the reaction tube kept at 520° C., a mixed gas of $N_2$ and steam (water) ($N_2$:steam=1.0:2.1 (molar ratio)) was allowed to pass therethrough at 154 mL/min for 30 minutes. Thereafter, indane (manufactured by Tokyo Chemical Industry Co., Ltd.), $N_2$ and steam (water) were each supplied to the reactor, and dehydrogenation reaction of indane was performed at a reaction temperature of 520° C. and 0.2 MPa. A raw material composition was indane:$N_2$:steam (water)=1.0:0.3:2.3 (molar ratio). The LHSV was set to 1.8 $h^{-1}$.

After elapse of 120 minutes and 180 minutes from the start of the reaction, a reaction product of the dehydrogenation reaction was collected from the tubular reactor. It is noted that the start of the reaction refers to a time when the supply of the raw material composition was started. The thus collected reaction product was analyzed by using a gas chromatograph equipped with a flame ionization detector (manufactured by Agilent, GC-7890, FID-GC). Based on a result obtained by the gas chromatograph, components (unit: % by mass) of the collected reaction product were quantitatively determined. Results are shown in Table 1.

Based on the molar numbers of indane and indene, the conversion rates of indane, the selectivities of indene, and the yields of indene each obtained when 120 minutes and 180 minutes had elapsed from the start of the reaction were calculated. It is noted that the conversion rate of indane is defined by the following expression (1), that the selectivity of indene is defined by the following expression (2), and that the yield of indene is defined by the following expression (3):

$$rC=\{1-(m1/m0)\} \times 100 \quad (1)$$

$$rS=\{m2/(m0-m1)\} \times 100 \quad (2)$$

$$rY=(m2/m0) \times 100 \quad (3)$$

rC of the expression (1) represents the conversion rate (%) of indane. rS of the expression (2) represents the selectivity (%) of indene. rY of the expression (3) represents the yield (%) of indene. In the expressions (1) to (3), m0 represents the molar number of indane in the raw material composition. In the expression (1) and (2), m1 represents the molar number of indane in the reaction product. In the expressions (2) and (3), m2 represents the molar number of indene in the reaction product.

Example 2

Example 2 was performed in the same manner as Example 1 except that the dehydrogenation catalyst A-2 was used instead of the dehydrogenation catalyst A-1. Results are shown in Table 1.

Example 3

Example 3 was performed in the same manner as Example 1 except that the dehydrogenation catalyst A-3 was used instead of the dehydrogenation catalyst A-1. Results are shown in Table 1.

Comparative Example 1

Comparative Example 1 was performed in the same manner as Example 1 except that the dehydrogenation catalyst B-1 was used instead of the dehydrogenation catalyst A-1. Results are shown in Table 1.

Comparative Example 2

Comparative Example 2 was performed in the same manner as Example 1 except that the dehydrogenation catalyst B-2 was used instead of the dehydrogenation catalyst A-1. Results are shown in Table 1.

Comparative Example 3

Comparative Example 3 was performed in the same manner as Example 1 except that the dehydrogenation catalyst B-3 was used instead of the dehydrogenation catalyst A-1. Results are shown in Table 1.

Comparative Example 4

Comparative Example 4 was performed in the same manner as Example 1 except that the dehydrogenation catalyst B-4 was used instead of the dehydrogenation catalyst A-1. Results are shown in Table 1.

Comparative Example 5

A tubular reactor was filled with 3.7 cc of a commercially available Fe—K catalyst (manufactured by Clariant Catalyst, Styromax-4), and a reaction tube was connected to a fixed bed flow reaction device. The reaction tube was heated to 520° C., and a mixed gas of $N_2$ and steam (water) ($N_2$:steam =1.0:2.1 (molar ratio)) was allowed to pass therethrough at 154 mL/min for 30 minutes. Thereafter, indane (manufactured by Tokyo Chemical Industry Co., Ltd.), $N_2$ and steam (water) were each supplied to the reactor, and dehydrogenation reaction of indane was performed at a reaction temperature of 520° C. and 0.2 MPa. A raw material composition was indane:$N_2$:steam (water)=1.0:0.3:2.3 (molar ratio). The LHSV was set to 1.8 $h^{-1}$.

After elapse of 120 minutes and 180 minutes from the start of the reaction, a reaction product of the dehydrogenation reaction was collected from the tubular reactor. It is noted that the start of the reaction refers to a time when the supply of the raw material composition was started. The thus collected reaction product was analyzed by using a gas chromatograph equipped with a flame ionization detector (manufactured by Agilent, GC-7890, FID-GC). Based on a result obtained by the gas chromatograph, components (unit: % by mass) of the collected reaction product were quantitatively determined. Results are shown in Table 1.

TABLE 1

|  |  | Example 1 | Example 2 | Example 3 | Comparative Example 1 | Comparative Example 2 | Comparative Example 3 | Comparative Example 4 | Comparative Example 5 |
|---|---|---|---|---|---|---|---|---|---|
| Catalyst Composition | Dehydrogenation Catalyst | A - 1 | A - 2 | A - 3 | B - 1 | B - 2 | B - 3 | B - 4 | Fe—K |
|  | Pt [mass %] | 1 | 1 | 1 | 3 | 1 | 0.5 | 1 | 0 |
|  | Sn [mass %] | 2.7 | 3.7 | 5.5 | 8.3 | 1.8 | 1.4 | 15.6 | 0 |
|  | Sn/Pt (atomic ratio) | 4.5 | 6.0 | 9.0 | 4.5 | 3.0 | 4.5 | 26.6 | — |
| Reaction Results | Indane Conversion Rate [%] after 120 min | 35 | 31 | 38 | 32 | 38 | 23 | 30 | 30 |
|  | after 180 min | 28 | 27 | 33 | 23 | 27 | 19 | 22 | 28 |
|  | Indene after 120 min | 91 | 85 | 90 | 91 | 79 | 76 | 87 | 29 |

TABLE 1-continued

|  |  | Example 1 | Example 2 | Example 3 | Comparative Example 1 | Comparative Example 2 | Comparative Example 3 | Comparative Example 4 | Comparative Example 5 |
|---|---|---|---|---|---|---|---|---|---|
| Selectivity [%] | after 180 min | 87 | 77 | 91 | 82 | 76 | 76 | 81 | 28 |
| Indene Yield [%] | after 120 min | 31 | 26 | 34 | 29 | 30 | 18 | 26 | 9 |
|  | after 180 min | 24 | 21 | 30 | 19 | 20 | 14 | 18 | 8 |
| (Indene Yield after 180 min/Indene Yield after 120 min) × 100 [%] |  | 77.4 | 80.8 | 88.2 | 65.5 | 66.7 | 77.8 | 69.2 | 88.9 |

INDUSTRIAL APPLICABILITY

According to the present invention, a production method for indene in which a side reaction is minimally caused and inane can be efficiently dehydrogenated can be provided as a novel production method for indene.

The invention claimed is:

1. A production method for indene, comprising a dehydrogenation step of obtaining a reaction product containing indene by contacting a raw material composition containing indane with a dehydrogenation catalyst,
    wherein the dehydrogenation catalyst comprises a support containing aluminum, and a group 14 metal element and platinum supported on the support,
    a content of the platinum in the dehydrogenation catalyst is 0.6 to 2.5% by mass based on a whole amount of the dehydrogenation catalyst, and
    an atomic ratio of the group 14 metal element to the platinum in the dehydrogenation catalyst is 4.0 to 20.0.

2. The production method according to claim 1, wherein the atomic ratio of the group 14 metal element to the platinum in the dehydrogenation catalyst is 7.0 to 20.0.

3. The production method according to claim 1, wherein the group 14 metal element is tin.

4. The production method according to claim 1, wherein the group 14 metal element and the platinum are supported on the support by using a metal source not containing a chlorine atom.

5. The production method according to claim 1, wherein a mole fraction of the indane in the raw material composition is 0.2 or more.

6. The production method according to claim 1, further comprising a raw material synthesis step of obtaining indane by dehydrogenation reaction of tetrahydroindene.

* * * * *